United States Patent
Abel et al.

(10) Patent No.: US 7,026,522 B2
(45) Date of Patent: Apr. 11, 2006

(54) PRODUCTION OF 2-AMINO-2-[2-(4-ALKYLPHENYL) ETHYL] PROPANE-1,3-DIOLS

(75) Inventors: Stephan Abel, Weil (DE); Tetsuro Fujita, Kyoto (JP); Ryoji Hirose, Hyogo (JP); Guido Jordine, Freiburg (DE); Tadashi Mishina, Osaka (JP)

(73) Assignee: Novartis AG, Basel (SE)

( * ) Notice: Subject to any disclaimer, the term of this patent is extended or adjusted under 35 U.S.C. 154(b) by 350 days.

(21) Appl. No.: 10/464,294

(22) Filed: Jun. 18, 2003

(65) Prior Publication Data

US 2003/0229251 A1    Dec. 11, 2003

Related U.S. Application Data

(60) Division of application No. 09/850,851, filed on May 8, 2001, now Pat. No. 6,605,744, which is a continuation of application No. PCT/EP99/08577, filed on Nov. 9, 1999.

(30) Foreign Application Priority Data

Nov. 11, 1998 (GB) .................... 9824705
Nov. 11, 1998 (GB) .................... 9824706

(51) Int. Cl.
 *C07C 22/00* (2006.01)
(52) U.S. Cl. .............. 570/195; 570/194; 570/201
(58) Field of Classification Search ............. 570/195, 570/194, 201
 See application file for complete search history.

(56) References Cited

U.S. PATENT DOCUMENTS 5,670,699 A    9/1997    Robl ................... 560/155

FOREIGN PATENT DOCUMENTS

| DE | 269 856 | 7/1989 |
|---|---|---|
| EP | 0 627 406 | 10/1993 |
| EP | 0 778 263 | 8/1995 |
| EP | 0 989 113 | 7/1998 |
| JP | 51115429 | 10/1976 |
| JP | 52108943 | 9/1977 |
| JP | 56145225 | 11/1981 |
| JP | 11310556 | 11/1999 |
| WO | WO 98/22100 | 5/1998 |

OTHER PUBLICATIONS

Bernstein et al., "Chemically Stable Homocinnamyl Analogues of the Leukotrienes: Synthesis and Preliminary Biological Evaluation", J. Med. Chem., vol. 29, pp. 2477-2483 (1986).
Derwent Abstracts, 2000-075377 (JP 11310556, Nov. 9, 1999).
Derwent Abstracts, 89368X (JP 51115429, Oct. 12, 1976).
Keszler et al., "Styryl-Telechelic Polyisobulytenes I. Synthesis of Linear and Tri-Arm Star Styrl-Telechelic Polyisobutylenes" (May 28, 1984) (Chemical Abstracts vol. 100, 22:192463f).
Derwent Abstracts, 1989-364565 (DD269856, Jul. 12, 1989).
Beilsteins Handbuch Der Organischen Chemie/* , vol. V, 4 Edition, Suppl. 3, pp 970, Springer Verlag, Berlin (1964).
Derwent Abstracts, 94279 D (JP 56145225, Nov. 11, 1981).
Dewent Abstracts, 76539Y (JP 52108943, Sep. 12, 1977).

*Primary Examiner*—Samuel Barts
(74) *Attorney, Agent, or Firm*—Susan Hess

(57) ABSTRACT

Disclosed is a process for the production of 2-amino-2-[2-(4-$C_{2-20}$-alkyl-phenyl)ethyl]propane-1,3-diols.

2 Claims, No Drawings

PRODUCTION OF 2-AMINO-2-[2-(4-ALKYLPHENYL) ETHYL] PROPANE-1,3-DIOLS

The present invention relates to a process for the production of 2-amino-2-[2-(4-$C_{2-20}$-alkyl-phenyl)ethyl]propane-1,3-diols, particularly 2-amino-2-[2-(4-octylphenyl)ethyl]propane-1,3-diol of formula

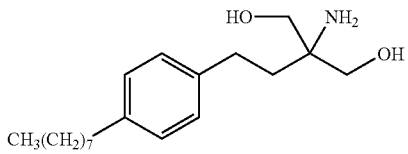

hereinafter defined as Compound A.

2-Amino-2-[2-(4-$C_{2-20}$-alkyl-phenyl)ethyl]propane-1,3-diols are disclosed in EP-A1-627,406 the relevant disclosure of which is incorporated herein by reference. On the basis of observed activity, e.g. as described in EP-A1-627,406, they have been found to be useful e.g. as immunosuppressants, e.g. in the prevention or treatment of acute allograft rejection or autoimmune diseases, or e.g. as described in WO 98/22100, in the prevention or treatment of xenograft rejection.

In accordance with the present invention, new processes for an improved production route of 2-amino-2-[2-(4-$C_{2-20}$-alkyl-phenyl)ethyl]propane-1,3-diols, particularly Compound A, in free form or in salt form, have now been found. It is to be understood hereinafter that the process steps of the invention may lead to 2-amino-2-[2-(4-$C_{2-20}$-alkyl-phenyl)ethyl]propane-1,3-diols in free form which may be converted into a salt form, or vice versa.

Accordingly, there is provided a process for preparing a 2-amino-2-[2-(4-$C_{2-20}$alkylphenyl)ethyl]propane-1,3-diol, in free form or in salt form, which process comprises g) reducing a compound of formula (20)

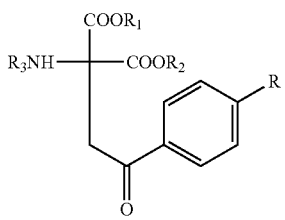

wherein R is $C_{2-20}$alkyl, each of $R_1$ and $R_2$, independently, is $C_{1-4}$alkyl and $R_3$ is a protecting group, followed by a treatment with $(R_4\text{—CO})_2O$ wherein $R_4$ is $C_{1-4}$alkyl, to obtain a compound of formula (21)

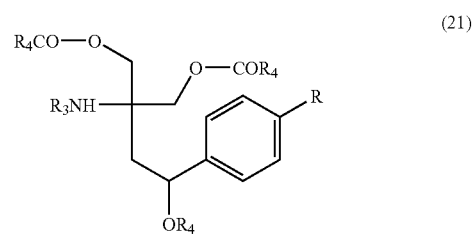

wherein R, $R_3$ and $R_4$ are as defined above; and i) treating the resulting compound of formula (21) with a basic compound to obtain a compound of formula (22)

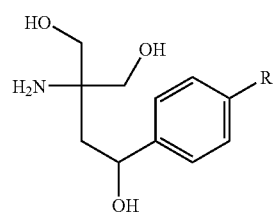

wherein R is as defined above; and j) hydrogenating the resulting compound (22)

Any alkyl group mentioned herein may be a straight or branched chain alkyl group. Preferably $C_{2-20}$alkyl is octyl, particularly straight chain.

Examples of protecting groups as $R_3$ are e.g. disclosed in "Protective Groups in Organic Synthesis", T. W. Greene, J. Wiley & Sons NY (1981), 219–287, e.g. acyl such as formyl, acetyl, benzoyl; alkoxycarbonyl e.g. t.-butyloxycarbonyl; allyloxycarbonyl; trityl; etc.

The reduction step g) may conveniently be performed using a reducing agent, e.g. $NaBH_4$. The following treatment with an anhydride may be effected e.g. with acetic anhydride, preferably in the presence of a neutralizing agent, e.g. an aliphatic or organic amine, e.g. pyridine.

Suitable basic compounds for use in step i) include an alkali metal hydroxide, e.g. NaOH, KOH or LiOH. Step i) may preferably be carried out in a polar solvent, e.g. an alcohol such as methanol, at reflux. Step j) may be effected in accordance with known hydrogenation methods, e.g. in the presence of a hydrogenation catalyst, e.g. Pd—C.

As an alternative to above process, a 2-amino-2-[2-(4-$C_{2-20}$alkylphenyl)ethyl]propane-1,3-diol in free form or in salt form may be prepared by h) hydrogenating a compound of formula (21) as defined above to obtain a compound of formula (9)

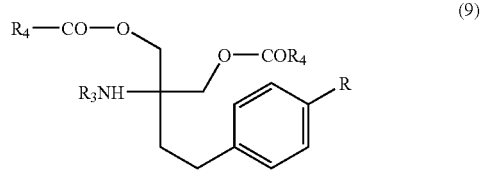

wherein R, $R_3$ and $R_4$ are as defined above; and

N) treating the resulting compound of formula (9) with a basic compound.

Steps h) and N) may be effected in accordance with methods known in the art, e.g. as disclosed above for steps j) and i), respectively, or in Examples 4 and 5 hereinafter.

According to a further embodiment of the invention, there is provided a process for preparing 2-amino-2-[2-(4-$C_{2-20}$alkylphenyl)ethyl]propane-1,3-diol, in free form or in salt form, which process, comprises x) reducing a compound of formula (20) as defined above, followed by a treatment with $(R_4CO)_2O$ to obtain a compound of formula (9) as defined above; and N) treating the resulting compound of formula (9) with a basic compound.

In process step x) the reduction may comprise either a hydrogenation step, e.g. as disclosed above for step (j), followed by a reduction step, e.g. as disclosed above for step (g), or a reduction step as diclosed for step (g) comprising an intermediary hydrogenation step [e.g. as disclosed for step (j)] prior to the anhydride $(R_4CO)_2O$ treatment. Step (N) may be carried out as indicated above.

In a further or alternative embodiment, the invention provides a process for preparing 2-amino-2-[2-(4-$C_{2-20}$alkylphenyl)ethyl]propane-1,3-diol, in free form or in salt form, which process comprises f) hydrogenating a compound of formula (20) as defined above or a compound of formula (20')

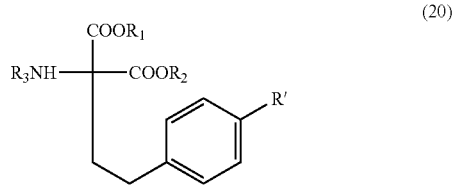
(20)

wherein $R_1$, $R_2$ and $R_3$ are as defined above, and R' is $C_{1-19}$—CO— to obtain a compound of formula (8)

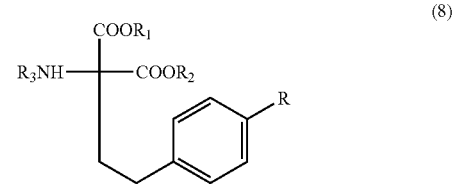
(8)

wherein R and $R_1$ to $R_3$ are as defined above; and

K) reducing the resulting compound of formula (8) followed by a treatment with $(R_4CO)_2O$ to obtain a compound of formula (9) as defined above; and N) treating the resulting compound of formula (9) with a basic compound.

Process steps (f) and (K) may be performed as disclosed above for (j) and (g), respectively. Alternatively, the reduction step (K) may be carried out in the presence of $Ca(BH_4)_2$. The latter may be generated by reaction of $NaBH_4$ with $CaCl_2$.

Compound of formula (20') may be prepared as disclosed in PCT/JP98/02998.

In a further or alternative embodiment, the invention further provides a process for preparing a 2-amino-2-[2-(4-$C_{2-20}$alkylphenyl)ethyl]propane-1,3-diol, in free form or in salt form, which process comprises g') reducing a compound of formula (20) as defined above under conditions to obtain a compound of formula (21')

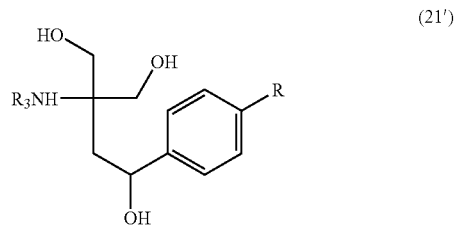
(21')

wherein R and $R_3$ are as defined above; and y) hydrogenating the resulting compound of formula (21') to obtain a compound of formula (21")

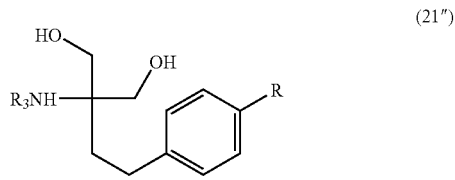
(21")

wherein R and $R_3$ are as defined above; and z) treating the resulting compound of formula (21") with a basic compound.

Process step (g') is a reduction carried out in the same manner as in step (g). Suitable reducing agents may be e.g. as disclosed above for step (g). Steps (y) and (z) may be carried out as disclosed above for steps (j) and (N).

As an alternative to above step (y), i') a compound of formula (21') as defined above may be reacted with a basic compound, e.g. an alkali metal hydroxide, to obtain a compound of formula (22) as defined above, which compound of formula (22) is then further treated as disclosed above for step (j).

Suitable alkali metal hydroxide may be e.g. LiOH.

Compound of formula (20), used as starting product in the preparation of a 2-amino-2-[2-(4-$C_{2-20}$alkylphenyl)ethyl] propane-1,3-diol, is novel and also forms part of the present invention, as well as its preparation. Compound of formula (20) may be obtained by a process comprising a) reacting a compound of formula (16)

(16)

wherein R is as defined above, with 2-bromoacetyl chloride to obtain a compound of formula (18)

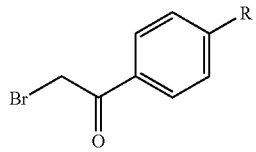

(18)

wherein R is as defined above; and
d) reacting the resulting compound of formula (18) with a compound of formula (2)

R₃NHCHCOOR₁
|
COOR₂

(2)

wherein R₁ to R₃ are as defined above.

Process step (a) may be performed in accordance with known bromoacetylation methods, e.g. in the presence of AlCl₃. Process step (d) may conveniently be effected in the presence of sodium ethylate, in an anhydrous solvent such as anhydrous ethanol, and under an inert atmosphere, e.g. nitrogen, e.g. as disclosed in Example 13. Compound of formula (18) used in above step (d) may also be prepared by reacting a compound of formula (16) as defined above, with acetyl chloride to obtain a compound of formula (18')

(18')

wherein R is as defined above, which compound of formula (18') is then brominated.

In a further or alternative embodiment, the invention further provides a process for preparing a 2-amino-2-[2-(4-C₂₋₂₀alkylphenyl)ethyl]propane-1,3-diol, in free form or in salt form, which process comprises
H) reacting a compound of formula (7)

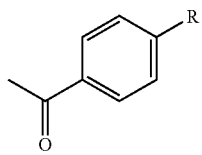

(7)

wherein R is as defined above, with a compound of formula (2) as defined above, to obtain a compound of formula (8) as defined above; and further submitting the resulting compound of formula (8) first to step (K) and then to step (N) as disclosed above.

Process step (H) may preferably be effected in the presence of sodium ethylate, e.g. as disclosed for step (d) above.

Compound of formula (7) used in process step (H) may be prepared by
c) iodinating a compound of formula (19)

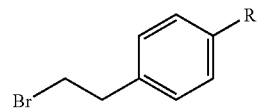

(19)

wherein R is as defined above; or
I) reducing a compound of formula (7')

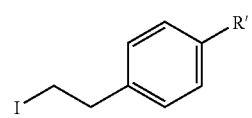

(7')

wherein R' is as defined above.

Process step (c) may conveniently be performed by reaction with an iodinating agent, e.g. an alkali metal iodide such as NaI or KI. Process step (I) may be carried out under acidic conditions, e.g. trifluoroacetic acid. Suitable reducing agents include e.g. triethylsilane.

Compound of formula (19), used as starting product in the preparation of 2-amino-2-[2-(4-C₂₋₂₀alkylphenyl)ethyl]propane-1,3-diol, is novel and also forms part of the present invention as well as its preparation. Compound of formula (19) may be obtained by
C) hydrogenating a compound of formula (10)

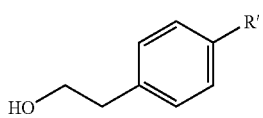

(10)

wherein R' is as defined above, to obtain a compound of formula (5)

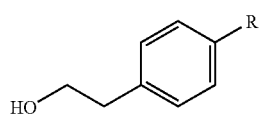

(5)

wherein R is as defined above; and
C') brominating the resulting compound of formula (5).

Process step (C) may be performed as disclosed e.g. for (j). Process step (C') may be carried out in accordance with methods known in the art, e.g. using a brominating agent, e.g. HBr, in the presence of a phase transfer-catalyst, e.g. an ammonium salt such as tricaprylmethylammonium halogenide, and further purification using e.g. aluminium oxide.

Compound of formula (19) may also be prepared by
b) reducing a compound of formula (18) as defined above.

Process step (b) may be carried out as disclosed for step (I) above.

Compound of formula (19) is useful to prepare the intermediary compound of formula (8) used in process step (K)

e) directly by reaction with a compound of formula (2) as defined above, preferably in the presence of a base, e.g. an alkali metal hydride such as NaH, or an alkali metal alkoxide, e.g. $C_2H_5$ ONa or t.-$C_4H_9$OK.

Process step e) may be carried out in accordance with known methods or e.g. as disclosed in Example 20.

According to the invention, Compound A is preferably prepared either starting from a compound of formula (19) and following above disclosed route: step (e)→step (K)→step (N);

or starting from a compound of formula (7) and following above disclosed route: step (H)→step (K)→step (N);

or starting from a compound of formula (20) or (20') and following above disclosed route: step (f)→step (K)→step (N).

The present invention also comprises each of the following steps disclosed above, respectively: step (b), step (c), step (C'), step (e), step (d), step (g'), step (g), step (x), step (f).

Examples of salts include salts with inorganic acids, such as hydrochloride, hydrobromide, and sulfate, salts with organic acids, such as acetate, lactate, succinate or tartarate, fumarate, maleate, benzoate, citrate, malate, methanesulfonate and benzenesulfonate salts. Preferred salt is the hydrochloride salt. 2-amino-2-[2-(4-$C_{2-20}$alkylphenyl) ethyl]-propane-1,3-diols, preferably Compound A, may be converted into the hydrochloride salt form in accordance with known methods, e.g. by addition of HCl to the last reaction step such as in step (j), or prior to recrystallization such as in step (N).

2-Amino-2-[2-(4-$C_{2-20}$alkylphenyl)ethyl]propane-1,3-diols and/or the intermediate compounds may be purified and/or separated by a conventional manner such as recrystallization, column chromatography, distillation, centrifugal separation, washing or drying.

The present Examples are illustrative of the invention.

EXAMPLE 1

Production of 2-acetamido-4-acetoxy-2-acetoxymethyl-4-(4-octylphenyl)butyl acetate (21) [Step (g)]

To a solution of diethyl acetamido-2-(4-octylphenyl)-2-oxoethylmalonate (20) (2.00 g) in methanol (8 ml) is added sodium borohydride (858 mg) and the mixture is stood at room temperature for 1.5 hr. The suspension is diluted with ethyl acetate and washed successively with 1N HCl, saturated aqueous NaHCO$_3$ solution and saturated brine. The ethyl acetate layer is dried over anhydrous MgSO$_4$ and concentrated. To the residue is added pyridine (4 ml)-acetic anhydride (8.8 ml), and the mixture is stood at room temperature overnight. To the reaction mixture is added ice water and the mixture is extracted with ethyl acetate and washed successively with 1N HCl, saturated aqueous NaHCO$_3$ solution and saturated brine. The ethyl acetate layer is dried over anhydrous MgSO$_4$ and concentrated. The residue is purified by silica gel column chromatography using hexane-ethyl acetate as eluent to give the title compound (21) as a colorless oil.

TLC Rf: 0.3 (hexane/ethyl acetate=1/2, silica gel 60F$_{254}$ plate)

IR (CCl$_4$) 3390, 2930, 2860, 1750, 1690, 1510, 1370, 1230, 1040 cm$^{-1}$.

$^1$H-NMR (500 MHz, CDCl$_3$) δ: 7.22 (2H, d, J=8.1 Hz, C$_6$H$_2$), 7.14 (2H, d, J=8.1 Hz, C$_6$H$_2$), 5.91 (1H, brs, NH), 5.84 (1H, dd, J=4.2 and 8.5 Hz, CH), 4.37 (1H, d, J=11.2 Hz, OCHa), 4.34 (1H, d, J=11.2 Hz, OCHb), 4.34 (2H, s, OCH$_2$), 2.56 (2H, t, J=7.8 Hz, PhCH$_2$), 2.54 (1H, dd, J=4.2 and 15.1 Hz, CHCHa), 2.36 (1H, dd, J=8.5 and 11.5 Hz, CHCHb), 2.10, 2.07 and 1.99 (each 3H, s, OAc), 1.90 (3H, s, NAc), 1.57 (2H, qui, J=7.8 Hz, CH$_2$), 1.32–1.23 (10H, m, CH$_2$×5), 0.87 (3H, t, J=7.1 Hz, CH$_3$)

FAB-MS m/z: 432 (M-AcOH+H)$^+$.

EXAMPLE 2

Production of 2-amino-2-(2-hydroxy-2-(4-octylphenyl)ethyl)propane-1,3-diol (22) [Step (i)]

2-Acetamido-4-acetoxy-2-acetoxymethyl-4-(4-octylphenyl)butyl acetate (21) (700 mg) is refluxed under heating for 5 hr in methanol (3.6 ml)/1N NaOH (7.2 ml). The reaction mixture is diluted with water and subjected to XAD-II column using water and methanol as eluents. The methanol eluate is concentrated to give the title compound (22) as a pale-yellow solid.

TLC Rf: 0.5 (chloroform/methanol/acetic acid/water=70/20/6/4, silica gel 60F$_{254}$ plate)

IR (KBr) 3340, 2930, 2850, 1470, 1040 cm$^{-1}$.

$^1$H-NMR (500 MHz, DMSO-d$_6$) δ: 7.20 (2H, d, J=8.1 Hz, C$_6$H$_2$), 7.10 (2H, d J=8.1 Hz, C$_6$H$_2$), 6.66 (1H, brs, CHOH), 4.83 (1H, dd, J=3.0 and 10.0 Hz, CH), 4.72 and 4.61 (each 1H, brs, OH), 3.42 (2H, s, OCH$_2$), 3.25 (1H, d, J=10.5 Hz, OCHa), 3.21 (1H, d, J=10.3 Hz, OCHb), 2.52 (2H, t, J=7.6 Hz, PhCH$_2$), 1.71 (2H, brs, NH$_2$), 1:55–1.51 (2H, m, CH$_2$), 1.51 (1H, dd, J=3.2 and 14.4 Hz, CHCHa), 1.47 (1H, dd, J=10.1 and 14.4 Hz, CHCHb), 1.27–1.23 (10H, m, CH$_2$×5), 0.85 (3H, t, J=7.1 Hz, CH$_3$)

FAB-MS m/z: 324 (M+H)$^+$

EXAMPLE 3

Production of 2-amino-2-[2-(4-octylphenyl)ethyl] propane-1,3-diol hydrochloride (Compound A in hydrochloride salt form) [Step (j)]

5% Pd/carbon (13 mg) is suspended in ethanol (0.5 ml) and a solution of 2-amino-2-[2-hydroxy-2-(4-octylphenyl) ethyl]propane-1,3-diol (22) (107 mg) in ethanol (4 ml)-1N HCl in ethanol (0.55 ml) is added. The mixture is stirred at room temperature for 10 days under 5 kg/cm$^2$ hydrogen pressurization. The reaction mixture is filtered and the filtrate is concentrated to Compound A (hydrochloride) as colorless crystals.

Decomposition: 260° C.

TLC Rf: 0.55 (chloroform/methanol/acetic acid/water=70/20/6/4, silica gel 60F$_{254}$ plate)

IR (KBr) 3400 (sh), 3250, 3050 (sh), 2910, 2850, 1580, 1520, 1470, 1060 cm$^{-1}$.

UVλ$_{max}$, (H$_2$O) nm (ε): 210.7(4709), 264(392.4), 272 (341.1)

$^1$H-NMR (500 MHz, DMSO-d$_6$) δ: 7.91 (3H, br s, NH$_3^+$), 7.09 (2H, d, J=8.5 Hz, C$_6$—H$_2$), 7.07 (2H, d, J=8.5 Hz, C$_6$—H$_2$), 5.38 (2H, br s, OH×2), 3.51 (4H, s, CH$_2$OH×2), 2.56 (2H, m, Ph-CH$_2$), 2.49 (2H, m, Ph-CH$_2$), 1.77 (2H, m, CH$_2$), 1.51 (2H, m, CH$_2$), 1.25 (10H, m, CH$_2$×5), 0.83 (3H, t, J=7.5 Hz, CH$_3$)

EIMS m/z: 276 (M-CH$_2$OH)$^+$, 117, 105

EXAMPLE 4

Production of 2-acetamido-2-acetoxymethyl-4-(4-octylphenyl)butyl acetate (9) [Step (h)]

5% Pd/carbon (20 mg) is suspended in ethyl acetate (0.5 ml) and a solution of 2-acetamido-4-acetoxy-2-acetoxymethyl-4-(4-octylphenyl)butyl acetate (21) (200 mg) in ethyl acetate (5 ml) and acetic acid (0.2 ml) are added. The mixture is stirred at room temperature for 6 days under 5 kg/cm$^2$ hydrogen pressurization. The reaction mixture is filtered and the filtrate is washed successively with saturated aqueous NaHCO$_3$ solution and saturated brine. The ethyl acetate layer is dried over anhydrous MgSO$_4$ and concentrated to give the title compound (9) as colorless crystals. m.p. 111.8° C.

TLC Rf: 0.4 (hexane/ethyl acetate=1/2, silica gel 60F$_{254}$ plate)

IR (KBr) 3330, 2910, 2850, 1740, 1650, 1550, 1470, 1390, 1260, 1240, 1050 cm$^{-1}$.

UV$\lambda_{max}$,(MeOH) nm ($\epsilon$): 217.6(4772), 259.0(305.7), 264.5(394.6), 272.8(368.6)

$^1$H-NMR (270 MHz, DMSO-d$_6$) $\delta$: 7.63 (1H, br s, NH), 7.07 (4H, s, C$_6$-H$_4$), 4.28 (2H, d, J=10.6 Hz, CHaOAc×2), 4.18 (2H, d, J=10.6 Hz, CHbOAc×2), ca. 2.5 (4H, m, Ph-CH$_2$×2), 2.02 (6H, s, OCOCH$_3$,×2), 1.94 (2H, m, CH$_2$), 1.85 (3H, s, NCOCH$_3$), 1.52 (2H, m, CH$_2$), 1.24 (10H, m, CH$_2$×5), 0.85 (3H, t, J=7.2 Hz, CH$_3$)

EIMS m/z: 433 (M)*, 373, 360, 300, 216, 157, 117, 105, 97

EXAMPLE 5

Production of 2-amino-2-[2-(4-octylphenyl)ethyl]propane-1,3-diol hydrochloride (Compound A in hydrochloride salt form) [Step (N)]

2-Acetamido-2-acetoxymethyl-4-(4-octylphenyl)butyl acetate (9) (7.37 kg) is refluxed under heating in methanol (51 L)-2N aqueous NaOH solution (34 L) for 6 hr. After cooling, the resulting precipitate is collected by filtration and washed thoroughly with water. The precipitate is dissolved in conc. HCl/ethanol (1:11) (20 L) and concentrated. The residue is recrystallized from ethyl acetate/ethanol to give Compound A (hydrochloride) as colorless crystals. The resulting Compound A has the same physico-chemical characteristics as indicated in Example 3.

EXAMPLE 6

Production of 2-acetamido-2-acetoxymethyl-4-(4-octylphenyl)butyl acetate (9) [Step (x)]

To a solution of diethyl acetamido-2-(4-octylphenyl)-2-oxoethylmalonate (20) (200 mg) in methanol (0.8 ml) is added sodium borohydride (85 mg) and the mixture is stood at room temperature for 2.5 hr. The reaction mixture is diluted with ethyl acetate and water, 1N HCl (2.24 ml) and acetic acid (0.26 ml) are added, followed by partitioning. The ethyl acetate layer is washed successively with saturated aqueous NaHCO$_3$ solution and saturated brine. The ethyl acetate layer is dried over anhydrous MgSO$_4$ and concentrated. The residue is stirred in ethanol (2 ml) in the presence of 5% Pd/Carbon (20 mg) and acetic acid (0.2 ml) for 8 days under 5 kg/cm$^2$ hydrogen pressurization. The reaction mixture is filtered through a membrane filter and the filtrate is concentrated.

The residue is dissolved in acetic anhydride (2.8 ml)-pyridine (1 ml), and the mixture is stood at room temperature overnight. The reaction mixture is poured into ice water and the precipitate is collected by filtration. The precipitate is recrystallized from hexane-ethyl acetate to give the title compound (9) as colorless crystals. The above-mentioned recrystallization filtrate is concentrated and purified by preparative TLC to give further the title compound (9) as colorless crystals. The resulting Compound (9) has the same physico-chemical characteristics as indicated in Example 4.

Alternatively compound (20) may be hydrogenated in ethanol in the presence of 5% Pd/C and then treated with NaBH$_4$ and then with acetic anhydride-pyridine as disclosed above.

EXAMPLE 7

Production of diethyl acetamido-2-(4-octylphenyl)ethylmalonate (8) [Step (f)]

Diethyl acetamido-2-(4-octylphenyl)-2-oxoethylmalonate (20) (200 mg) is stirred at room temperature for 6 days in ethanol (2 ml) in the presence of 5% Pd/carbon (20 mg) under 5 kg/cm$^2$ hydrogen pressurization. The reaction mixture is filtered and the filtrate is concentrated. The residue is dissolved in ethyl acetate and washed successively with saturated aqueous NaHCO$_3$ solution and saturated brine. The ethyl acetate solution is dried over anhydrous MgSO$_4$ and concentrated to give the title compound (8). m.p. 61° C.

Alternatively diethyl acetamido-2-(4-octylphenyl)ethylmalonate (8) is prepared by hydrogenation of diethyl acetamido-2-(4-octan-1'-oylphenyl)-ethylmalonate in the presence of 5% Pd/carbon as disclosed above.

Compound (8) has the same physico-chemical characteristics as indicated above.

TLC Rf: 0.6 (hexane/ethyl acetate=1/1, silica gel 60F$_{254}$ plate).

IR (KBr) 3300, 2920, 2850, 1750, 1650, 1520, 1220, 1200 cm$^{-1}$.

UV$\lambda_{max}$, (MeOH) nm ($\epsilon$): 219.1(5017), 259.2(303.5), 264.5(392.4), 272.7(357.7).

$^1$H-NMR (270 MHz, DMSO-d$_6$) $\delta$: 8.32 (1H, br s, NH), 7.08 (2H, d, J=7.9 Hz, C$_6$—H$_2$), 7.02 (2H, d, J=7.9 Hz, C$_6$—H$_2$), 4.13 (4H, q, J=7.3 Hz, OCH$_2$CH$_3$×2), 2.52 (4H, m, Ph-CH$_2$×2), 2.37 (2H, m, CH$_2$), 1.94 (3H, s, COCH$_3$), 1.52 (2H, m, CH$_2$), 1.24 (10H, m, CH$_2$×5), 1.15 (6H, t, J=7.3 Hz OCH$_2$CH$_3$×2), 0.85 (3H, t, J=6.6 Hz, CH$_3$)

EIMS m/z: 388 (M-OCH$_2$CH$_3$)$^+$, 318, 301, 244, 217, 171, 143.

EXAMPLE 8

Production of 2-acetamido-2-acetoxymethyl-4-(4-octylphenyl)butyl acetate (9) [Step (K)]

To a solution of diethyl acetamido-2-(4-octylphenyl)ethylmalonate (8) (1.37 kg) in methanol (5.5 L) is added sodium borohydride (720 g), and the mixture is stirred at room temperature for 2 hr. The suspension is diluted with ethyl acetate, and washed successively with 4N HCl, saturated aqueous NaHCO$_3$ solution and saturated brine. The ethyl acetate layer is dried over anhydrous magnesium sulfate and concentrated. To the residue are added pyridine (3 L) and acetic anhydride (12 L), and the mixture is stirred at room temperature overnight. The reaction mixture is poured into ice water and the precipitated crystals are collected by filtration. The precipitate is recrystallized from hexane/ethyl acetate (2/1) to give the title compound (9) as colorless crystals. The resulting Compound (9) has the same physico-chemical characteristics as indicated in Example 4.

Alternatively, the reduction of Compound (8) may be carried out using $NaBH_4$ and $CaCl_2$, e.g. in aqueous ethanol.

EXAMPLE 9

Production of 2-acetamido-2-[2-hydroxy-2-(4-octylphenyl)ethyl]propane-1,3-diol (21') [Step (g')]

Diethyl 2-acetamido-2-[2-(4-octylphenyl)-2-oxoethyl] malonate (20) (4 g) is dissolved in methanol (150 ml) and sodium borohydride (tablet, 1.64 g) is added. The mixture is stirred for 1 hr under heating at 50° C. The solvent is evaporated and the residue is extracted with ethyl acetate. The extract is washed with brine and dried over sodium sulfate. The solvent is evaporated to give the title compound (21') as colorless crystals. m. p.118–119° C.

IR (KBr): 3228, 2927, 1640, 1566, 1071 $cm^{-1}$.

$^1$H-NMR ($CDCl_3$): 0.86 (3H, t, J=6 Hz), 1.18–1.33 (10H, m), 1.48–1.64 (2H, m), 1.57 (2H, bs), 1.80 (1H, dd, J=8 Hz, J=10 Hz), 2.02 (3H, s), 2.34 (1H, d, J=10 Hz), 2.56 (2H, t, J=6 Hz), 3.39–3.47 (1H, m), 3.54–3.62 (1H, m), 3.68–3.80 (2H, m), 4.11 (1H, br. s), 4.85 (1H, d, J=7 Hz), 6.96 (1H, br. s), 7.14 (2H, d, J=8 Hz), 7.23 (2H, d, J=8 Hz)

MS (EI) m/z: 365 ($M^+$)

EXAMPLE 10

Production of 2-amino-2-[2-hydroxy-2-(4-octylphenyl)ethyl]propane-1,3-diol (22) [Step (i')]

2-Acetamido-4-(4-octylphenyl)-2-hydroxymethylbutane-1,4-diol (21') (0.73 g) is dissolved in methanol (10 ml). Thereto is added a solution of LiOH (0.86 g) in water (10 ml), and the mixture is refluxed under heating for 2 hr. The reaction mixture is cooled and extracted with ethyl acetate. The organic layer is washed with brine and dried over sodium sulfate. The solvent is distilled away and the mixture is purified by silica gel column chromatography to give the title compound (22) as a colorless and amorphous powder. The resulting Compound (22) has the same physico-chemical characteristics as indicated in Example 2.

EXAMPLE 11

Production of 2-bromo-4'-octylacetophenone (18) [Step (a)]

To a suspension of aluminum chloride (3.88 g) and bromoacetyl chloride (4.56 g) in dichloromethane (5 ml) is added dropwise over 1 hr a solution of octyl-benzene (16) (5.0 g) in dichloromethane (7 ml) under ice-cooling, and the mixture is stirred under ice-cooling for 1 hr. The reaction mixture is poured into ice water and extracted with ethyl acetate. The organic layer is washed successively with HCl, saturated aqueous $NaHCO_3$ solution and saturated brine, dried over anhydrous $MgSO_4$ and concentrated to give the title compound (18) as a colorless oil.

TLC Rf: 0.4 (hexane/ethyl acetate=20:1, silica gel $60F_{254}$ plate)

IR ($CCl_4$) 2930, 2860, 1680, 1610, 1430, 1280, 1180, 1010 $cm^{-1}$.

$^1$H-HMR (500 MHz, $CDCl_3$) δ: 7.90 (2H, d, J=8.5 Hz, $C_6H_2$), 7.29 (2H, d, J=8.5 Hz, $C_6H_2$), 4.44 (2H, s, $BrCH_2$), 2.67 (2H, t, J=7.6 Hz, $PhCH_2$), 1.63 (2H, qui, J=7.1 Hz, $CH_2$), 1.32–1.26 (10H, m, $CH_2$×5), 0.88 (3H, t, J=7.1 Hz, $CH_3$)

$^{13}$C-NMR (500 MHz, $CDCl_3$) δ: 190.93, 149.95, 131.60, 129.05, 128.89, 36.06, 31.82, 31.01, 30.97, 29.38, 29.24, 29.19, 22.63, 14.08

EIMS m/z: 312 and 310 $(M)^+$, 217, 91

EXAMPLE 12

Production of 2-bromo-4'-octylacetophenone (18)

4'-Octylacetophenone (18') [Step (a')]

Aluminum chloride (22.6 g) is suspended in dichloroethane (500 ml) and octylbenzene (16) (21.5 g) is added at room temperature. To the mixture is added acetyl chloride (8.87 g) under ice-cooling. The mixture is stirred at room temperature overnight. The reaction mixture is poured into ice water and extracted with ether. The organic layer is washed with brine and dried over sodium sulfate. The solvent is evaporated to give 4'-octylacetophenone (18') as a colorless oil.

2-Bromo-4'-octylacetophenone (18) [Step (a")]

To a solution of 4'-octylacetophenone (18') (23.9 g) in acetic acid (100 ml) is added hydrogen bromide-acetic acid solution (25%, 34 ml) under ice-cooling, which is followed by dropwise addition of bromine (5.3 ml). The mixture is heated to 30° C. and stirred for 3 hr. The solvent is distilled away and the mixture is purified by silica gel column chromatography to give 2-bromo-4'-octylacetophenone as colorless crystals.

m.p. 33–34° C.

The resulting Compound (18) has the same physico-chemical characteristics as indicated in Example 11.

EXAMPLE 13

Production of diethyl acetamido-2-(4-octylphenyl)-2-oxoethylmalonate (20) [Step (d)]

A solution of 2-bromo-4'-octylacetophenone (18) (5.0 g), diethyl acetamidomalonate (3.85 g) and sodium ethylate (1.20 g) in anhydrous ethanol (50 ml) is refluxed under heating under nitrogen atmosphere for 6 hr. The reaction mixture is diluted with hexane/ethyl acetate, washed with water, dried over anhydrous $MgSO_4$ and concentrated. The residue is purified by silica gel column chromatography using hexane/ethyl acetate as eluent to give the title compound (20) as a pale-yellow oil.

TLC Rf: 0. 5 (hexane/ethyl acetate=1/1, silica gel $60F_{264}$ plate)

IR ($CCl_4$): 3420, 2930, 2860, 1750, 1690, 1610, 1490, 1350, 1230, 1200 $cm^{-1}$.

$^1$H-NMR (500 MHz, $CDCl_3$) δ: 7.87 (2H, d, J=8.3 Hz, $C_6H_2$), 7.25 (2H, d, J=8.3 Hz, $C_6H_2$), 7.11 (1H, s, NH), 4.26 and 4.40 (each 2H, q, J=7.1 Hz $OCH_2$), 4.23 (2H, s, $COCH_2$), 2.65 (2H, t, J=7.8 Hz, $PhCH_2$), 1.96 (3H, s, Ac), 1.61 (2H, qui, J=7.3 Hz, $CH_2$), 1.30–1.22 (10H, m, $CH_2$×5), 1.23 (6H, t, J=7.1 Hz, $CH_3$×2), 0.87 (3H, t, J=7.1 Hz, $CH_3$)

FAB-MS m/z: 448 $(M+H)^+$

EXAMPLE 14

Production of 2-(4-octylphenyl)ethyl bromide (19) [Step (b)]

To a solution of 2-bromo-4'-octylacetophenone (18) (1.0 g) in trifluoroacetic acid (2.5 ml) is added triethylsilane (1.12 ml) under ice-cooling, and the mixture is stirred at room temperature for 2 hr. The reaction mixture is poured into ice water and hexane and saturated aqueous $NaHCO_3$ solution are added, which is followed by partitioning. The hexane layer is washed with saturated brine, dried over anhydrous $MgSO_4$ and concentrated. The residue is purified by silica gel column chromatography using hexane as eluent to give the title compound (19) as a colorless oil.

TLC Rf: 0.5 (hexane, silica gel $60F_{254}$ plate)

IR ($CCl_4$) 2930, 2860, 1510, 1470 $cm^{-1}$.

$^1$H-NMR (500 MHz, $CDCl_3$) δ: 7.15 (2H, d, J=8.3 Hz, $C_6H_2$), 7.12 (2H, d, J=8.3 Hz, $C_6H_2$), 3.56 (2H, t, J=7.8 Hz, $BrCH_2$), 3.14 (2H, t, J=7.8 Hz, $PhCH_2$), 2.59 (2H, t, J=7.8 Hz, $PhCH_2$), 1.61 (2H, qui, J=7.6 Hz, $CH_2$), 1.35–1.27 (10H, m, $CH_2×5$), 0.89 (3H, t, J=7.3 Hz, $CH_3$)

EIMS m/z: 298 and 296 (M)$^+$, 217, 197 and 199, 117, 105, 91

EXAMPLE 15

Production of 2-(4-octylphenyl)ethyl iodide (7) [Step (c)]

To a solution of 2-(4-octylphenyl)ethyl bromide (19) (99 mg) in 2-butanone (5 ml) is added NaI (126 mg) and the mixture is refluxed under heating for 3 hr. The reaction mixture is diluted with hexane and washed successively with saturated aqueous sodium sulfite solution and saturated brine. The hexane layer is dried over anhydrous $MgSO_4$ and concentrated to yield the title compound (7) as a colorless oil.

TLC Rf: 0.6 (hexane, silica gel $60F_{254}$ plate)

IR ($CCl_4$) 2930, 2860, 1510, 1470,1170 $cm^{-1}$.

1H-NMR (500 MHz, $CDCl_3$) δ: 7.13 (2H, d, J=8.1 Hz, $C_6H_2$), 7.10 (2H, d, J=8.1 Hz, $C_6H_2$), 3.33 (2H, t, J=7.6 Hz, $ICH_2$) 3.15 (2H, t, J=7.8 Hz, $PhCH_2$), 2.57 (2H, t, J=7.8 Hz, $PhCH_2$), 1.60 (2H, qui, J=7.8 Hz, $CH_2$), 1.34–1.26 (10H, m, $CH_2×5$), 0.88 (3H, t, J=6.6 Hz, $CH_3$)

EIMS m/z: 344 (M$^+$), 245, 217, 119, 117, 91, 57, 43

EXAMPLE 16

Production of diethyl acetamido-2-(4-octylphenyl)ethylmalonate (8) [Step (H)]

To a solution of diethyl acetamidomalonate (277 g) and sodium ethylate (86.6 g) in anhydrous ethanol (850 ml) is added a solution of 2-(4-octylphenyl)ethyl iodide (7) (146 g) in anhydrous tetrahydrofuran (533 ml), and the mixture is refluxed under heating for 6 hr. The reaction mixture is concentrated and partitioned between water and hexane, and the hexane layer is washed three times with water. The obtained hexane layer is dried over anhydrous magnesium sulfate and concentrated. The residue is recrystallized from hexane to give the title compound (8) as colorless crystals. The resulting Compound (8) has the same physico-chemical characteristics as indicated in Example 7.

EXAMPLE 17

Production of 2-(4-octylphenyl)ethyl iodide (7) [Step (I)]

To a solution of 4'-(2-iodoethyl)octanophenone (200 g) in trifluoroacetic acid (319 ml) is added triethylsilane (195.7 ml) under ice-cooling, and the mixture is stirred at room temperature for 2 hr. The reaction mixture is concentrated, and the residue is distilled away under reduced pressure to give the title compound (7) as a pale-red oil. The resulting Compound (7) has the same physico-chemical characteristics as indicated in Example 15.

EXAMPLE 18

Production of 2-(4-octylphenyl)ethanol (5) [Step (C)]

5% Pd/carbon (0.6 g) is added to a solution of 2-(4-octanoylphenyl)ethanol (10) (30 g) in abs. ethanol (150 ml). The mixture is stirred at room temperature for 2.5 hrs under 0.1 bar hydrogen. The reaction mixture is filtered and the filtrate is concentrated to afford compound (5) as a clear pale yellow oil.

IR (NaCl): 3300, 2926, 2854, 1513, 1466, 1046 $cm^{-1}$.

$^1$H-NMR (200 MHz, $CDCl_3$) δ: 7.12 (4H,s,$C_6H_4$); 3.87 (2H,t,J=7.7 Hz, $CH_2O$); 2.85 (2H, t, J=7.7 Hz, Ph-$CH_2$); 2.59 (2H, t, J=7.8 Hz, Ph-$CH_2$); 1.61 (2H, q, J=7.8 Hz, $CH_2$); 1.40–1.15 (10H, m, $CH_2×5$); 0.89 (3H, t, 7.3 Hz, $CH_3$)

EIMS m/z: 234 (M+), 203, 135, 105

EXAMPLE 19

Production of 2-(4-octylphenyl)ethyl bromide (19) [Step (C')]

2-(4-octylphenyl)ethanol (5) (46.9 g) is added within 10 min to an aqueous solution containing 3.05 g $Na_2SO_3$, 252.9 g 48% HBr and 3.2 g tricaprylmethylammonium chloride. The reaction mixture is heated to 100° C. for 18 to 22 hours with stirring. The resulting 2-phase mixture is cooled to room temperature, diluted with toluene (150 ml) and the aqueous phase is then removed. The organic phase is washed twice with a volume of 100 ml of a 9% $NaHCO_3$ solution. The organic phase is treated with basic aluminium oxide, then filtered. The filter residue is washed with toluene (50 ml) and evaporated to yield compound (19) as a clear pale yellow oil. The resulting Compound (19) has the same physico-chemical characteristics as indicated in Example 14.

EXAMPLE 20

Production of diethyl acetamido-2-(4-octylphenyl)ethylmalonate (8) [Step (e)]

60% NaH in oil (9.65 g) is added portionwise to a solution of diethyl acetamidomalonate (58.5 g) in dimethylformamide (240 ml) at such a rate to keep the temperature below 10° C. The resulting mixture is stirred for 90 min., the temperature being allowed to increase to room temperature. To this mixture is added dropwise within 15 min. a solution of 2-(4-octylphenyl)ethyl bromide (19) (40 g) in dimethylformamide (40 ml). The reaction mixture is heated to ca. 80°

C. within ca. 25 min. and further stirred for ca. 3–5 hrs. After cooling to room temperature, water (280 ml) is added and the resulting mixture is further stirred until a beige precipitate is formed. The mixture is adjusted to pH 7 with 10% $H_2SO_4$. After cooling to ca. 2° C., the residue is filtered, washed with 200 ml water and then recrystallized in heptane to yield compound (8) as colorless crystals. The resulting compound (8) exhibits the same physico-chemical characteristics as indicated in Example 7.

What is claimed is:

1. A process for preparing a compound of formula (19)

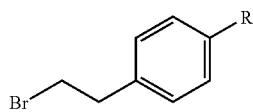

(19)

wherein R is $C_{2-20}$alkyl, comprising

C) hydrogenating a compound of formula (10)

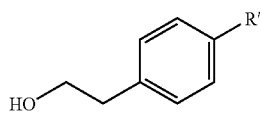

(10)

wherein R' is $C_{1-19}$alkyl-C=O, to obtain a compound of formula (5)

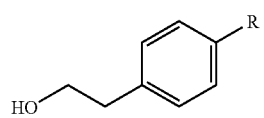

(5)

wherein R is $C_{2-20}$alkyl; and

C') brominating the resulting compound of formula (5).

2. A process according to claim 1, wherein C1-19 alkyl of C1-19 alkyl-C=O is heptyl and each of C2-20alkyl and R is octyl.

* * * * *